United States Patent [19]

Wang

[11] Patent Number: 5,044,001
[45] Date of Patent: Aug. 27, 1991

[54] METHOD AND APPARATUS FOR INVESTIGATING MATERIALS WITH X-RAYS

[75] Inventor: Chia-Gee Wang, Millwood, N.Y.

[73] Assignee: Nanod Ynamics, Inc., Houston, Tex.

[21] Appl. No.: 541,261

[22] Filed: Jun. 20, 1990

Related U.S. Application Data

[63] Continuation-in-part of Ser. No. 129,476, Dec. 7, 1987, abandoned.

[51] Int. Cl.[5] .............................................. G21K 7/00
[52] U.S. Cl. ....................................... 378/43; 378/45
[58] Field of Search .................... 378/43, 45, 46, 53; 250/310, 306, 307, 305

[56] References Cited

U.S. PATENT DOCUMENTS

| | | | |
|---|---|---|---|
| 2,843,751 | 7/1958 | Botty et al. | 378/43 |
| 4,382,181 | 5/1983 | Wang | 378/45 |
| 4,588,891 | 5/1986 | Saito | 250/310 |
| 4,988,872 | 1/1991 | Nagatsuka et al. | 250/310 |
| 4,990,778 | 2/1991 | Norioka | 250/310 |

Primary Examiner—Edward P. Westin
Assistant Examiner—Kim-Kwok Chu
Attorney, Agent, or Firm—Ladas & Parry

[57] ABSTRACT

A method of investigating materials, especially biological specimens, utilizes a focused accelerated beam of electrons within an evacuated chamber, striking a metal foil within the chamber and exposing a specimen outside the evacuated chamber to x-rays generated in the metal foil. The apparatus of the invention functions as an x-ray microscope and in a preferred embodiment, as a scanning x-ray microscope.

26 Claims, 5 Drawing Sheets

METHOD AND APPARATUS FOR INVESTIGATING MATERIALS WITH X-RAYS

This is a continuation-in-part of copending application Ser. No. 07/129,476 filed on Dec. 7, 1987 now abandoned.

BACKGROUND OF THE INVENTION

1. Field of the Invention

This invention relates to a method of investigating materials using x-rays and to apparatus therefor. More particularly, the invention relates to investigating biological specimens under ambient conditions of the environment by means of an x-ray microscope (XM). In a preferred embodiment, a novel scanning x-ray microscope (SXM) is provided and utilized in the method of the invention.

From the time of the discovery of x-ray radiation, x-rays have been utilized in many different ways for the investigation of materials including biological materials. Microscopes have been of great importance in the investigation of both biological and other materials. Optical microscopes are limited in resolution by the wavelength of the photons in a beam of visible light. The electron microscope (EM) was developed using the electromagnetic lens to focus the electrons. Electrons can have extremely short wavelengths which enables the EM to have very high magnification and greatly improved resolution compared with optical microscopes. Electrons are also employed in a scanning electron microscope (SEM), which operates in a different way from the EM. An SEM employs a beam of electrons focused to a spot having a diameter of several nm which is scanned over the surface of a sample in a pattern generating secondary electrons which are detected and amplified for each pixel to collectively compose a picture of the surface of the sample. Compared with an optical microscope, a far better resolution and depth of field is obtained.

However, investigation of materials with an EM or SEM requires examining the specimens in an evacuated environment for the passage of electrons, as well as treatment of the specimens. For investigation with an EM, a very thin specimen must be prepared and stained with heavy metals. The sample for a SEM requires coating with heavy metals.

2. Description of Related Art

A scanning x-ray microscope (SEM) is disclosed in U.S. Pat. No. 4,317,036 granted on Feb. 23, 1982 to Chia-Gee Wang. This patent discloses that prior attempts to construct x-ray microscopes were based on equipping electron microscopes with x-ray detectors and that such a system can function as an x-ray microscope with scanning electron detection. Among the factors stated to cause the prior XM to become complex and expensive was the need for a vacuum housing for the electron beam and the specimen. The invention of this patent was directed towards a more simple system in which a beam of x-rays was attempted to be focused onto a small spot for scanning the beam over a specimen, without the use of vacuum. However, it has been found that the necessary precise focusing of the x-ray beam is complex and difficult in many cases. Accordingly, there is a need in the art for a system which avoids the difficulty of focusing an x-ray beam, while providing a means of analyzing materials or specimens under normal conditions not involving the application of a vacuum to the specimens.

Many types of equipment have been developed to utilize x-rays for investigation or analysis of materials. One such type is an x-ray analyzer, electron-micro probe, generally described in "Van Nostrand's Scientific Encyclopedia", Sixth Edition, pages 3041–3044, the disclosure of which is incorporated herein by reference. This instrument is mainly used for metal-lurgical studies but properly prepared biological specimens may also be analyzed. An optical microscope is used to identify a point of interest on the specimen to be analyzed. An electron beam is focused on such point on the specimen and resulting x-rays are detected and processed to provide quantitative data. In the instrument of this reference, the electron beam is focused directly onto the specimen, both the beam and the specimen being under vacuum. The reference further discloses the production of electron beams and detectors for detection of x-rays.

The field is generally reviewed in "X-ray Microscopy", Proceedings of the International Symposium, Gottingen, Fed. Rep. of Germany, Sept. 14–16, 1983, edited by G. Schmal and D. Rudolph, Springer-Verlag, 1984, the contents being given on pages vii–ix.

X-rays have also been used for the detection of atoms in biological specimens using monochromatic x-rays, as disclosed in U.S. Pat. No. 4,239,966 issued on Dec. 16, 1980 and U.S. Pat. No. 4,382,181 issued on May 3, 1983, both issued to Chia-Gee Wang.

An article in SCIENCE, vol. 237, Aug. 14, 1987, pages 723–724 discusses current research in scanning x-ray microscopy. The article states that biological material in an aqueous environment has been imaged by scanning x-ray microscopy employing a synchrotron light source. X-rays from the light source are focused with use of a Fresnel zone plate. The system is described as not being perfected in view of lengthy time to record images so that dynamic processes cannot be studied and because of noise in the images. Future attempts are to involve brighter soft (long wavelength) x-ray sources, but the article states that it is yet to be demonstrated that cell structures will always survive this soft and intense x-ray dose. Also disclosed in the article are other prior techniques such as contact x-ray micrography in which shadowgraphs of samples illuminated by an x-ray beam are recorded by lithographic means and a transmission electron microscope is used to magnify the image. Prior work has also involved the x-ray analog of an optical microscope. Both the contact method and the optical analog method utilize an intense beam of soft x-rays from a synchrotron light source. The use of a scanning instrument is suggested because of the potential to employ a lower radiation dose and to follow changes within living cells, but the disadvantage of scanning is explained as involving the need to use a very bright x-ray source.

SUMMARY OF THE INVENTION

In accordance with the present invention there is provided a method of investigating materials by the use of x-rays, which comprises focusing an accelerated beam of electrons in an evacuated space on a metal foil facing said evacuated space, wherein the metal foil has thickness of less than about 0.1 $\mu$m, the electron beam focused on said metal foil having a beam diameter of less than about 1000 Å incident on the metal foil, said metal foil being supported on a first surface of a support substrate which is substantially transparent to x-rays and has a second surface outside said evacuated space, said focused electron beam generating x-rays in said metal foil, placing a specimen of a material to be investigated adjacent to said second surface of said substrate in a position exposed to the x-rays generated in said metal foil, and selectively detecting from said specimen only x-rays selected from those having a peak energy or an energy close to the peak energy.

Also provided according to the invention is an apparatus for investigating materials by the use of x-rays, which comprises a chamber for being maintained under vacuum, said chamber having a wall which has an aperture in which is mounted a support substrate composed of a material substantially transparent to x-rays, said support substrate having a first surface facing the interior of said chamber and a second surface facing outside said chamber, said first surface of the support substrate having thereon a metal foil, said metal foil having a thickness of less than about 0.1 $\mu$m, exposed to the interior of the chamber, means for focusing a beam of electrons within said chamber on said metal foil to a beam diameter of less than about 1000 Å incident on the metal foil, means for positioning a specimen outside said chamber adjacent to said second surface of the support substrate, and at least one x-ray detector positioned to detect x-rays leaving said specimen, said x-ray detector being an energy dispersive x-ray detector capable of selecting and recording a narrow range of peak energy and energies close to peak energy.

Figure 7:
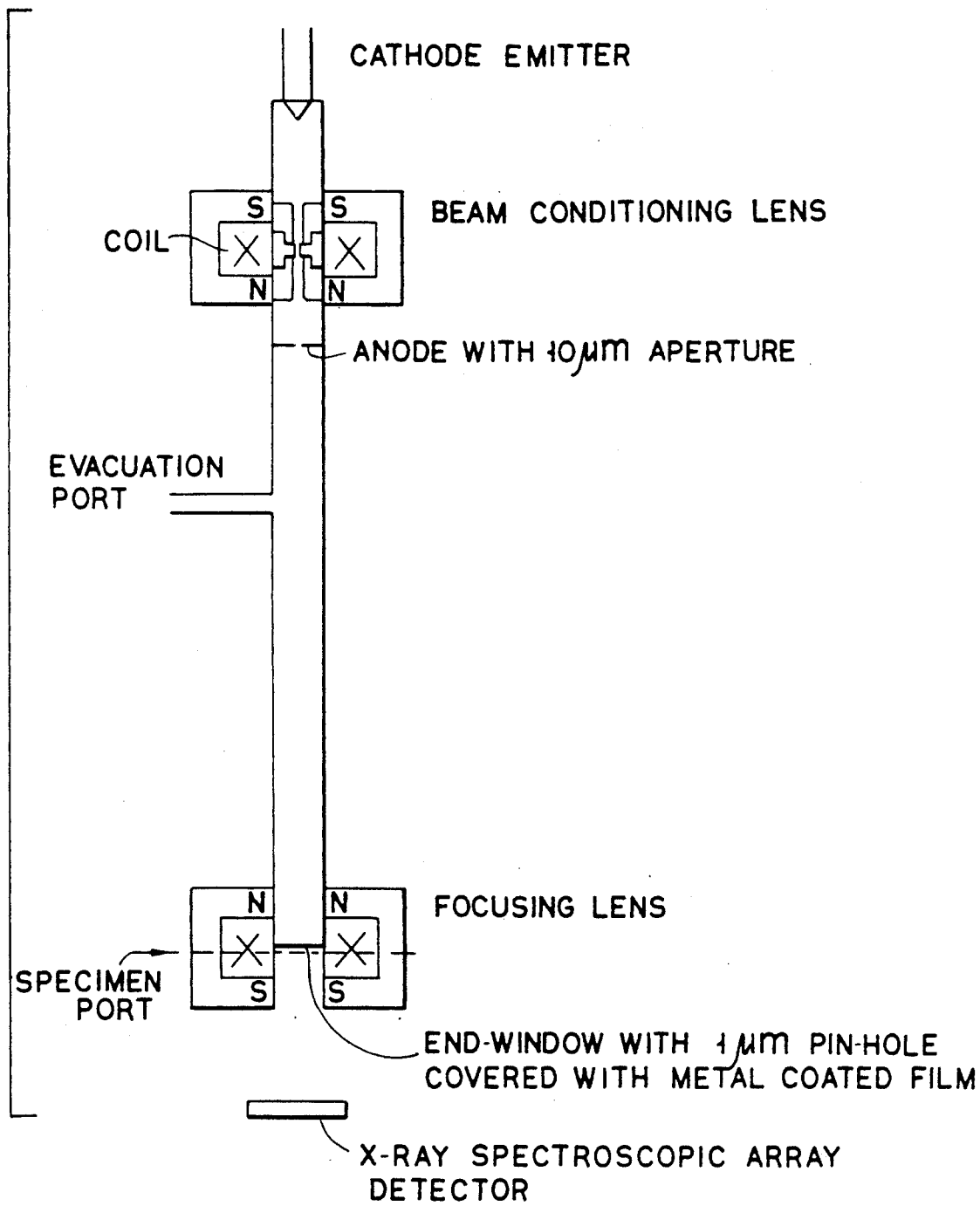

FIG. 7 as a cross-sectional illustration of an end window x-ray tube in accordance with the present invention.

Figure 8:
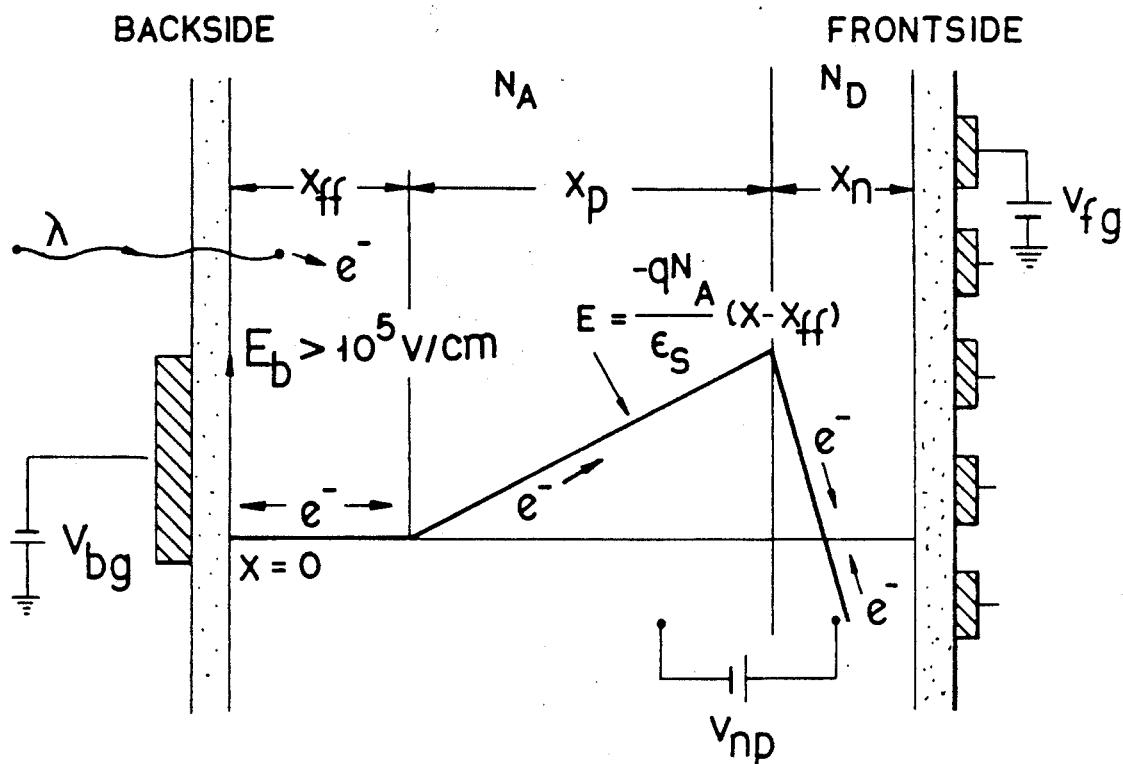

FIG. 8 is a cross-sectional illustration of a charge-coupled device (CCD) configuration, from a paper by Janesick, JR et al. Optical Engineering 26, 156;1987.

DESCRIPTION OF THE PREFERRED EMBODIMENTS

The invention of the EM in 1932 provided biomedical scientists with a very important instrument for studying cells in fine detail. The resulting great progress in cell biology set the stage for the most important discoveries of modern science, namely, the identification of DNA as the carrier of genetic information by Avery and associates in 1944, and the discovery of the structure of DNA and the basis of the genetic code by Watson and Crick in 1953. Molecular biology emerged to become a powerful new discipline, and particularly with the introduction of recombinant DNA techniques in recent years, has undergone an explosive growth.

However, important biological and biochemical information, such as details of cellular dynamic processes cannot be obtained from EM images which are of a treated specimen at a fixed point in time.

A biologically viable peptide or protein, for example, often cannot readily be created by simply synthesizing it from its corresponding DNA sequence. Much information regarding cellular controls is unknown, and fine details of cellular processes, particularly of biochemical transport, can only be studied by indirect means. A convenient instrument for directly viewing cellular dynamic processes under physiological conditions instead of only displaying images fixed in time under artificial conditions, clearly would be of great value.

By means of the present invention, biological specimens can be viewed using an XM or SXM in an ambient environment without subjecting the specimens to large radiation dosage or evacuation. Dynamic processes such as biochemical transport can thus be viewed live under controlled temperature, pH, and chemical concentration. Increasingly smaller targets could be resolved with improvements in beam resolution. At 1000 Å (0.1 $\mu$m), for example, certain viruses can be resolved and their movements followed; at 100 Å, certain membrane receptors may become visible and their interactions identified; at 10 Å, even individual amino acids may become visible and the peptide chemistry studied live.

Potential other applications in the fields of chemistry, materials sciences, geology and geochemistry are also numerous. Even at an x-ray beam resolution of 0.1 $\mu$m the method and apparatus of the present invention can serve to examine, for example, chemical transport in a microchip at the level of submicron structure, or phase transition in a material at a submicron domain.

According to the method of the present invention, materials such as biological specimens are investigated with use of x-rays. The specimen is able to be investigated under ambient conditions of the environment without being subjected to high radiation dosage or evacuation. The x-rays which are used to investigate the specimen are produced by focusing an accelerated beam of electrons in an evacuated space or chamber onto the surface of a metal foil. The metal foil can be a thin layer, film or coating of a metal on a substrate. The metal foil should be thin and may have a thickness of 10 $\mu$m or below, and preferably is thinner, having a thickness of 5 $\mu$m or below. More preferably, the foil has a thickness less than 1 $\mu$m. The metal of the foil may be silver, aluminum or an aluminum alloy, or any metal which similarly emits bremsstrahlung x-ray photons upon being subjected to an electron beam (e-beam). It is desirable for the foil to be con-structed so that it will conduct and dissipate heat and electrons. For this purpose, the foil can be connected to a heat sink or a conductor for removal of electrons.

The beam of electrons typically is accelerated to an energy within the range of 1-20 keV.

Electrons from the beam of electrons focused on the metal layer are slowed down as they enter the metal region and emit bremsstrahlung x-ray photons. The electrons encounter multiple scattering in the foil and produce photons from each scattering event. Photons created by multiple scatterings are emitted in all directions and their energy levels range from the peak e-beam energy downwards thereby greatly broadening the spatial resolution of the e-beam. In many uses of the invention, beam broadening is an important problem for the SXM and is considered subsequently in the present description. The emitted x-rays substantially comprise x-rays having a wavelength equal to or below 5 Å or an energy equal to or greater than 2 keV.

The substrate which is used to support the metal foil is made of a material which is substantially transparent to x-rays and substantially non-transparent to electrons. Such a material may be made of beryllium or preferably a polymer. More preferably, the substrate is made of an organic polymer.

The electron beam is focused as a point or spot on the surface of the metal foil, and the area of x-ray peak production is not much bigger than the electron beam spot. However, the resolution may range twice or more the size of the electron spot. Therefore, it is preferred that the beam of electrons should be focused to a beam diameter of less than about 1,000 Å incident on the metal foil. Preferably the beam is focused to a beam diameter of less than about 100 Å and more preferably less than about 10 Å incident on the metal foil. A size for the probe of electrons (the spot size) of as small as 5 Å may be achieved.

The metal foil which faces the evacuated space is supported on a first surface of the support substrate which is substantially transparent to x-rays, the support substrate having a second surface which faces outside the evacuated space. Thus, when a specimen of the material to be investigated is positioned adjacent to the second surface of the substrate, the specimen becomes exposed to the x-rays generated in the metal foil but is outside the evacuated space and thus is not subjected to a vacuum. In this position, the specimen is subjected to x-rays generated in the metal foil, which are emitted in all directions. Some of the emitted x-rays pass through the substrate and also are transmitted through the specimen. In addition, the x-rays entering the specimen cause the generation of flurorescent x-rays from atoms in the specimen.

Figure 3:
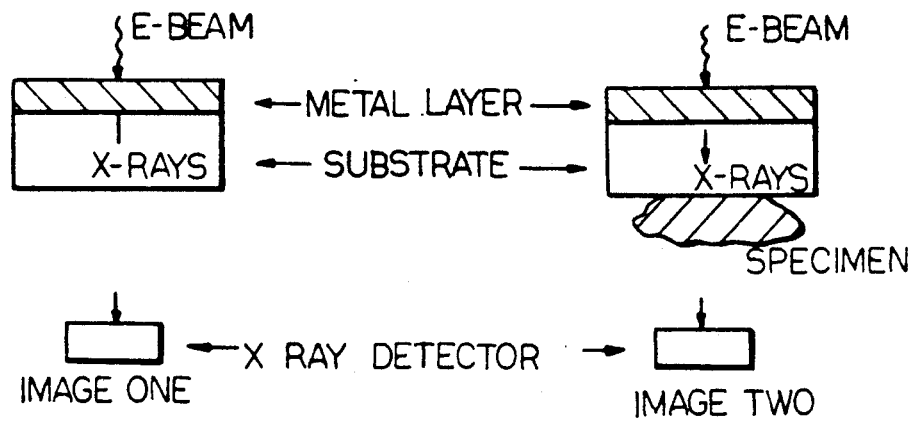
FIG. 3 is a schematic representation of the production of images in accordance with the present invention.

X-rays from said specimen which are characteristic of properties of a region of said specimen are selectively detected. The selective detection can involve the selection of either fluorescent x-rays or transmission x-rays, or both. Transmission x-rays characteristic of properties or structure of a region of the specimen can be selectively detected in the presence of other x-rays representing noise. A selection of transmission x-rays characteristic of the specimen may be done in the following way. The produced x-ray photons, which are far more transparent to the foil than the electrons, leave an aluminum (or other metal) foil and its substrate to interact with the specimen, while a significant number of electrons cannot reach the specimen because the foil and the substrate are substantially non-transparent to electrons. An x-ray detector, positioned to receive x-rays of a certain direction and solid angle, preferably is employed to register the x-rays with and without the specimen. Without the specimen in place, the detector simply reports the "image" of an aluminum layer plus its substrate. As shown in FIG. 3, with the specimen placed in the path of the x-ray beam, the detector reports the foil image plus the specimen. The difference of the two images, from digitized substraction, becomes the designated x-ray image of the specimen alone.

Thus, in accordance with a preferred embodiment of the present invention, the x-rays from said specimen are selectively detected by obtaining a first signal from x-rays detected from said specimen, obtaining a second signal from x-rays detected from the metal foil and substrate in the absence of said specimen, and digitally substracting the second signal from the first signal, thereby obtaining a digitally encoded image of a region of the specimen.

In many cases, it is preferred to limit the thickness of the specimen to 50 μm or below, and preferably to a thickness of 1-20 μm.

Beam broadening is a problem to be considered in many instances, depending upon the use which is intended.

Figure 4:
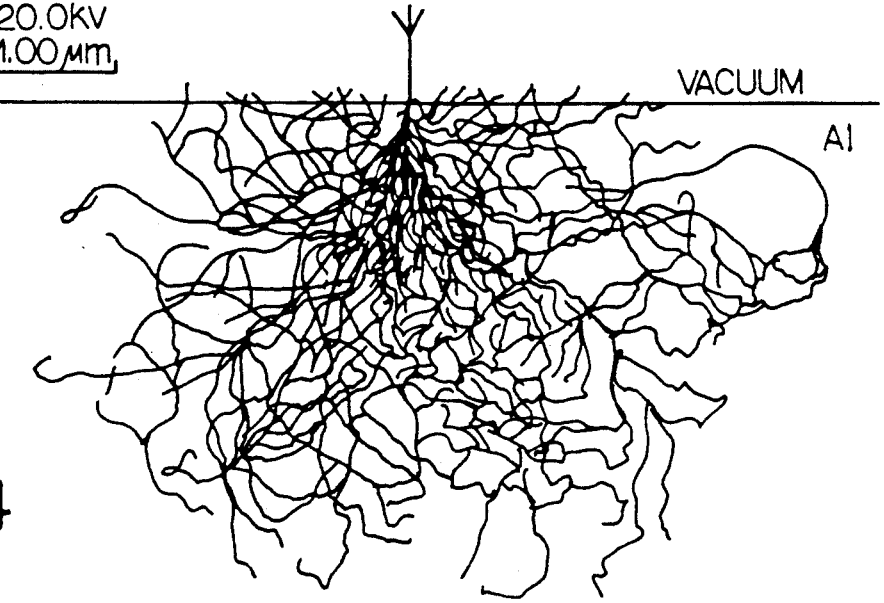
FIG. 4 is a monte carlo computer simulation of the electron trajectories in an aluminum layer.
Figure 5:
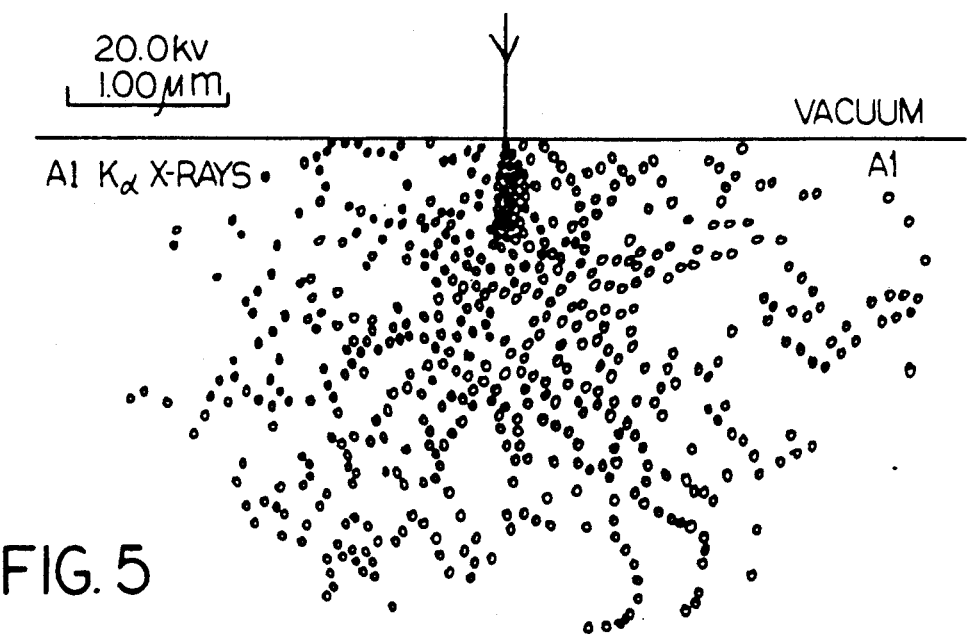
FIG. 5 is a computer simulation of x-ray productions resulting from the electron trajectories depicted in FIG. 4.

FIG. 4 depicts a monte carlo computer simulation of the electron trajectories in an aluminum layer of one micrometer from a point source of 20 keV, and FIG. 5 shows the resultant x-ray productions, the source of these simulations being R. B. Bolon of the General Electric Company, New York.

It can be seen from the monte carlo simulation that an intense region of scattering occurs in a dimension of about 0.1 micrometer. In the present invention, the metal foil, e.g. an aluminum layer, preferably is coated onto an organic substrate. The substrate provides mechanical strength and is useful to support metal layers of different chosen thicknesses. The substrate must provide mechanical strength without generating intense x-rays. The coated aluminum layer facing the incident electron beam generates x-rays, conducts charge, and dissipates heat. The monte carlo calculation in FIGS. 4 and 5 assumed a point electron beam to result in a broadened x-ray beam. If the incident electron beam has a finite beam size, this broadened x-ray spot must include one-half of the point broadening to all directions of the finite electron beam size, resulting in a point broadening in addition to the electron beam size.

As electrons are slowed down in the foil through multiple scattering, each scattering gives rise to bremsstrahlung radiation. The distribution of scattering energies is a well defined function of the electron beam energy as well as the foil thickness. If x-rays are selected from only the peak energy, the x-ray beam size would essentially be confined to the incident electron beam spot because no multiple scattering could take place to degrade the beam definition without first degrading the electron energy. A energy dispersive x-ray detector can easily discriminate and select only the peak energy for registration, thereby recording only those x-rays generated from the electron beam spot. A properly positioned axial symmetric diffractor, such as a graphite crystal, also helps to channel higher energy photons from a larger solid angle to reach the detector while blocking the passage of lower energy photons. Another way to channel the distribution of x-rays mainly toward the peak energy is to reduce the thickness of the metal foil so that multiple scatterings in the foil are initially reduced.

Therefore, in the step of detecting x-rays from the specimen, it is a preferred embodiment of the present invention to detect principally only x-rays selected from those having a peak energy or an energy close to the peak energy.

In a preferred embodiment of the invention, the position of the accelerated electron beam is moved so that an area of the metal foil is scanned by the beam of electrons, thereby providing a SXM. The scanning movement of the electron beam is done by conventional techniques as are known in the operation of a SEM. This may be done, for example, by utilizing a modified SEM wherein the electron beam is accelerated and scanned, but the specimen is placed outside of the SEM adjacent to an aperture holding a metal foil exposed to the scanning electron beam and supported by a support substrate having a surface outside the SEM against which the specimen is located. In that way, signals representative of an image of a region of the specimen are obtained, by the processing of detected x-rays representative of different parts of the region obtained during the scanning process. A digitally encoded image of a region of the specimen is obtained and amplified, and may be displayed, such as by means of an electron beam in a cathode ray tube. As is conventional, the electron beam in said cathode ray tube is scanned in synchronization with the scanning of the beam of electrons directed to the metal foil.

By selective detection of fluorescent photons, the obtained image can be element specific. For this purpose an energy dispersive x-ray detector is used which is also energy discriminating. Transmission x-rays leave the specimen in a forward direction (downstream direction of the e-beam) and would represent noise or background when it is desired to selectively detect fluorescent photons. Fluorescent x-rays do not have a forward intensity peak. To enhance the signal-to-noise ratio of the fluorescent x-ray signals, the fluorescent x-ray detector should be placed outside of the main e-beam path. It is a further preferred embodiment of the invention to selectively detect fluorescent x-rays emitted from the specimen.

Fluorescent x-rays characteristic of a specific chemical element may be detected and a signal produced which is representative of the concentration of the specific chemical element in the specimen. Thus, the energy selectivity of the x-ray detector can be used to analyze the chemical composition of the specimen, i.e., selected to report the characteristic fluorescent x-rays. In order to retain the beam definition where only the peak x-ray energy is detected, the electron beam energy should be controlled to be near a major absorption edge of the element in question. In other words, each element of interest in the specimen should be examined with an electron beam energy set at near the characteristic energy of the element for a good beam definition. Searching through a series of elements thus requires a dynamic energy scan, and this energy scan is independent of the positional scan described above for the SXM of the present invention. This method can be used as a chemical scan of sub-micron dimension with or without the positional variation (scanning the electron beam over a region of the metal foil). A static spot analysis of chemical composition can be obtained without positional scanning, i.e. with the XM of the present invention, and provides important information. Repeated over a time interval, the changes in elemental or chemical composition of a region or a spot in the specimen can be determined.

Accordingly, in the aspect of the present invention wherein fluorescent x-rays characteristic of a specific chemical element are detected, the energy of the accelerated beam of electrons is preferably maintained at substantially the same as the energy of the fluorescent x-rays characteristic of the specific chemical element. Moreover, in this embodiment of the invention, the energy of the accelerated beam of electrons may be sequentially changed to provide a series of different energies corresponding to different energies of fluorescent x-rays characteristic of the different chemical elements, with production of signals representing the concentration of a plurality of such chemical elements in the specimen. The method of the invention further includes obtaining different signals over a period of time which represent the changing concentrations of those different chemical elements in the specimen. By further combining the technique of scanning an area of the metal foil with the production of signals over a period of time representative of changing concentrations of different chemical elements, the resulting signals produced are representative of changing concentrations of different elements throughout a region of the specimen.

For image formation representing chemical analysis, a dynamic electron beam energy scan may be employed together with gate variation of the x-ray detector. The dynamic energy scan controls the anode voltage of an electron gun and associated electromagnetic lenses as well as the detector window. These controls are useful to maintain a good x-ray beam definition.

The apparatus of the invention will now be described with reference to the drawings.

Figure 1:
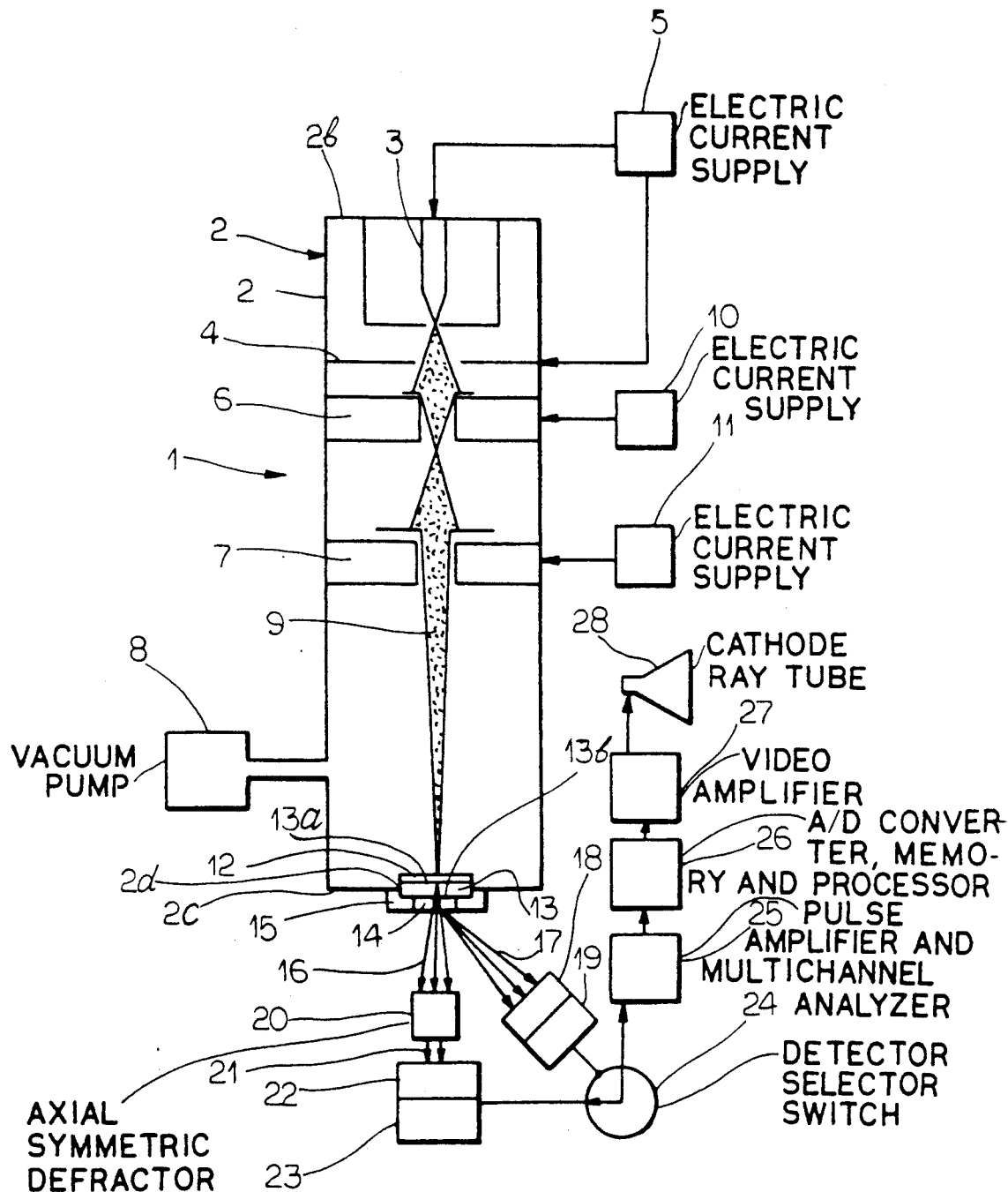
FIG. 1 is a schematic elevational view partly in cross-section of an x-ray microscope of the present invention.
Figure 2:
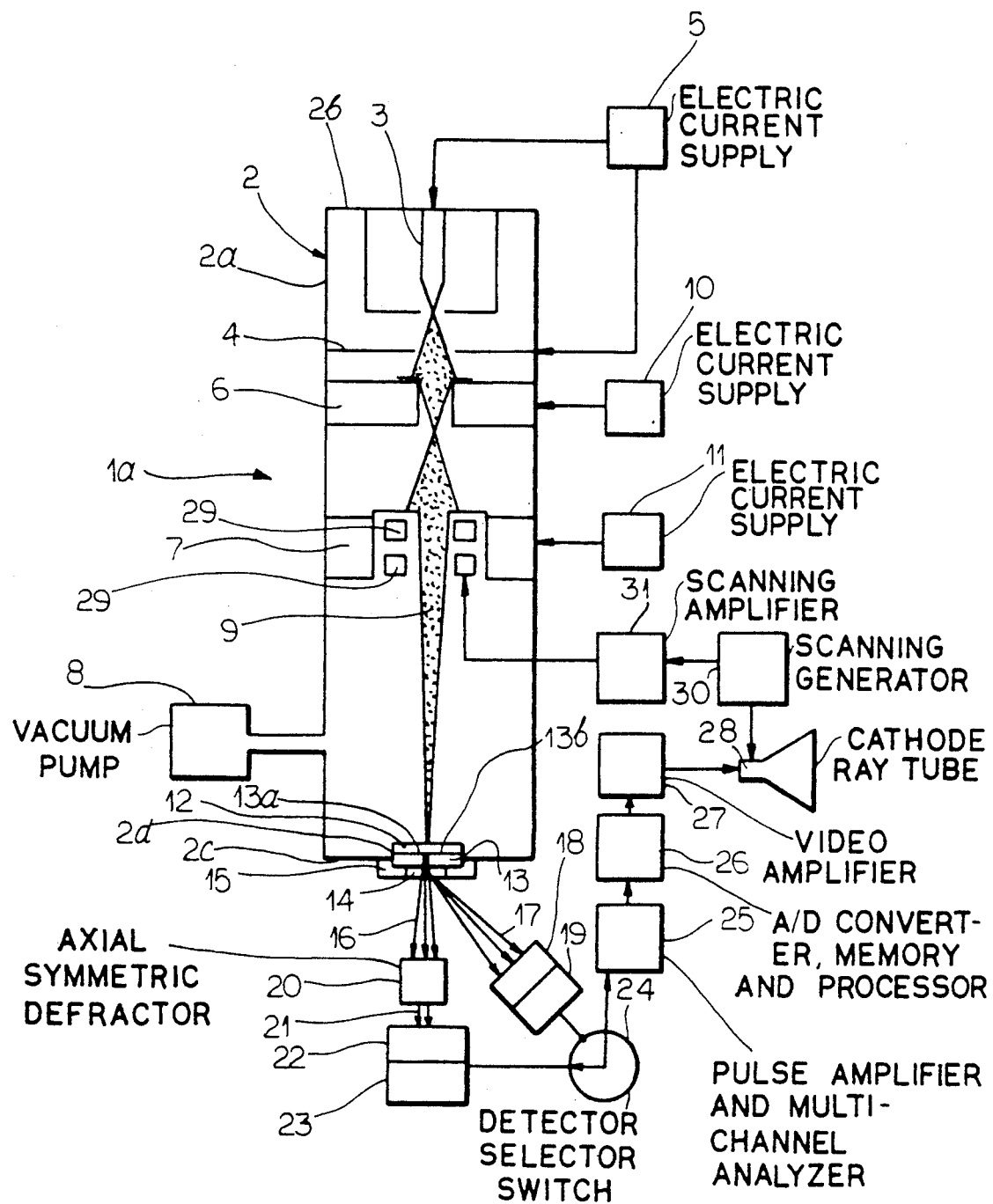
FIG. 2 is a schematic elevational view partly in cross-section of a scanning x-ray microscope of the present invention.

FIG. 1 illustrates an embodiment of an XM, shown generally as 1, of the present invention and FIG. 2 illustrates a SXM embodiment, shown generally as 1a, of the present invention. As shown in both FIGS. 1 and 2, the apparatus of the invention comprises a chamber 2 which comprises a generally elongated chamber housing 2a and at opposite ends of said housing a first end wall 2b and a second end wall 2d. The second end wall 2c has an aperture 2d. A support substrate 13 is mounted in or adjacent to aperture 2c, the support substrate 13 being composed of a material substantially transparent to x-rays and having a first surface 13a facing the interior of chamber 2 and a second surface 13b facing outwardly of said chamber 2. A metal foil 12 is disposed on first surface 13a of said substrate 13. The metal foil is a thin layer but for clarity is exaggerated in thickness in the FIGS. 1 and 2. Metal foil 12 thus is in a position exposed to the interior of chamber 2. The chamber is capable of being evacuated and maintained under vacuum, for example by means of vacuum pump 8.

The apparatus of the invention further comprises means for producing and accelerating a beam of electrons 9 within said chamber 2 along a beam path. The electron beam may be produced by an electron gun 3 and accelerated by anode 4, with electric current supply 5 supplying filament heating power to the electron gun 3 and high voltage power to anode 4, through electric current conductors shown in FIGS. 1 and 2 by arrows. The beam of electrons alternatively may be generated outside of chamber 2 by other means.

Said chamber 2 preferably is an elongated hollow body, with the means for producing and accelerating the beam of electrons 9 being adjacent to the first end wall 2b, and the support substrate 13 being mounted in second end wall 2c, the electron beam path extending along a lengthwise axis in a downstream direction from the means for producing and accelerating the beam of electrons to the metal foil 12.

Means is provided for focusing the beam of electrons 9 within said chamber. The means for focusing may comprise electromagnetic condenser lens 6 and objective lens 7, electric current supply 10 for the condenser lens and electric current supply 11 for the objective lens, the electric current conductors being depicted by arrows.

Means such as specimen holder 15 is provided for positioning a specimen 14 (shown exaggerated in thickness) outside said chamber 2 adjacent to the second surface 13b of substrate 13. Specimen holder 15 may comprise a cup for specimens dispersed in water or other liquid, or a clamp for solid phase specimens.

X-ray detector 18 for fluorescent x-rays 17 and/or x-ray detector 22 for transmission x-rays 16 are disposed in a location where they are capable of detecting x-rays leaving said specimen 14. Cooperating with each x-ray detector 18 and 22 is a preamplifier 19 and 23, respectively. X-ray detector selector switch 24 is provided to divert the output of one or the other preamplifier to amplification, signal processing and display units. Also included within the scope of the invention, although not shonw, is a switching arrangement whereby the output of both detectors may be simultaneously used. Further, additional x-ray detectors may be employed, or only one detector may be provided.

X-ray detector 22 is located downstream from the means for positioning a specimen, in the path of axial x-rays 21 transmitted from specimen 14, and said means for positioning a specimen and said x-ray detector 22 are disposed in alignment with the lengthwise axis of chamber 2.

X-ray detector 18 is positioned out of alignment with the lengthwise axis of chamber 2, and is substantially out of the path of x-rays 16 transmitted through said specimen 14, and is in the path of fluorescent x-rays 17 emitted from specimen 14. Although x-ray detector 18 for fluorescent x-rays is shown in FIGS. 1 and 2 as preferably being disposed outside of chamber 2, this detector may instead be positioned inside chamber 2 or disposed outside chamber 2 adjacent to or in an aperture in chamber housing 2a (not shown in the figures), said aperture being sealed by a window or detector window which is transparent to x-rays. Detector 18 can be placed in the alternative positions indicated or it can be maintained in the position shown in the drawings and an additional fluorescent x-ray detector can be placed in the alternative positions.

The x-ray detectors are preferably energy dispersive and energy discriminating. X-ray detector 22 of this type is thereby capable of selecting and recording a narrow range of peak energy and energies close to peak energy, to assist in the recording of only the x-rays generated from the electron beam spot.

An axial symmetric defractor 20 may also be included, to direct x-rays 21 having energies close to peak energy towards x-ray detector 22, while blocking the passage of lower energy x-rays. The defractor 20, which may comprise a graphite crystal, is disposed between the specimen holder 15 and x-ray detector 22, in axial alignment with the lengthwise axis of chamber 2.

For recording or displaying information obtained from detected x-ray signals, the apparatus of the invention may include means for amplifying a signal representative of the detected x-rays. For this purpose, the output from the preamplifier 19 or 23 is conducted by detector selector switch 24, to a pulse amplifier and multi-channel analyzer 25. The signal from analyzer 25 is transmitted to A/D (analog-to-digital) converter, memory and processor 26, the output of which may be conducted for display to a video amplifier 27 which controls a display unit comprising CRT (Cathode ray tube) 28. The CRT display unit may be a computer monitor.

Energy dispersive x-ray detectors usually require a multi-channel analyzer to distiguish one pulse height from another. But with the use of personal computers, the multi-channel analyzer and discriminator, together with the A/D converter, digitized image memories and processing can all be processed by a PC-AT with a modification board. The high speed of an AT unit is needed in order to complete the data processing in a reasonable time. The imaged output can be handled on the AT computer by using a high-resolution extended graphics board in combination with a high-resolution color monitor which produces a color image, with each separate color representing a different element. The minimum resolution desirably should be 640×400 pixels.

A preferred embodiment of the apparatus of the present invention is a SXM as illustrated in FIG. 2. The SXM apparatus as illustrated further comprises means for scanning the beam of electrons 9 over an area of the metal foil 12. This is accomplished by further modification of the FIG. 1 apparatus, as shown in FIG. 2, by the provision of a scanning coil 29 which can sweep the electron beam in a scanning pattern generated by a scanning generator 30, the output of which is directed to a scanning amplifier 31 which in turn is connected to scanning coil 29. The output of the scanning generator 30 also is directed to CRT display unit 28 so that the cathode ray tube is scanned in synchronization with the scanning of the metal foil.

X-ray photons cannot be refracted while entering a medium of different density, and therefore cannot be focused like the usual optical lens. Soft x-rays can, however, reflect at a grazing incidence from a conductive and smooth surface, and this phenomenon was first utilized by Kirkpatrick to build a microscope with a pair of grazing mirrors before the invention of electron microscopes. Grazing reflection of soft x-rays was applied most successfully in the Uhoro astrophysical satellites. A number of attempts of microscope design following the Uhoro approach have met with limited success. The focus to a sub-micro dimension remains a technical barrier. An x-ray funnel pulled from a capillary tube with its inner surface coated by metal coating was disclosed in the above-mentioned Wang U.S. Pat. No. 4,317,036.

Regarding the x-ray sources, the brightness of the source from a pin-hole, for example, compensates for the lack of optical focusing, and the brightest pin-hole source by far is that of synchrotron radiation. A pulsed discharge from a plasma pinch or the stripping of inner electrons from an intense laser field can both give rise to a concentrated and bright x-ray spot. A large reflective surface constructed with alternatively absorbing and transmitting layers can help focus x-ray photons at a particular wavelength. A review of various attempts in x-ray microscopy can be found in "Ultrasoft X-ray microscopy: Its Application to Biological and physical Sciences", Annals of the New York Academy of Sciences Volume 342; 1980.

Figure 6:
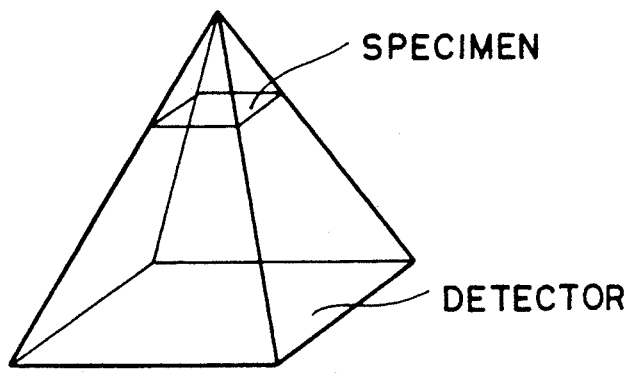
FIG. 6 is a diagram showing a geometric relationship of specimen and detector.

It is preferred to use a very bright x-ray source with a highly concentrated beam spot and a CCD (charge-coupled device) as the spectroscopic as well as imaging detector. The specimen is placed between the source and the detector to form a shadow as image from the detector. Without evacuation to the specimen, wet biological specimens can thus be studied in their physiological state. FIG. 6 illustrates an outline of the geometric arrangement.

THE X-RAY SOURCE

As shown in FIG. 7, x-rays are generated similarly to that of a usual end-window x-ray tube where electrons accelerate toward an end-window coated with a conductive layer and x-rays generated from the said layer emerge from the window. The end window layer serves to seal the vacuum, to conduct the heat and the charges, and to generate the x-rays. Spot size of the known x-ray generation is usually at millimeter or large. In an embodiment of the present invention the e-beam is focused to a spot of the order to 500 Å, and the conductive coating is at thickness of the order of the spot size. A low Z substrate, such as beryllium, is used to cover the end-window. As the end-window can be as small as one micron pin-hole, even a very thin layer can support the vacuum stress. The thin end-window layer is made of many ultra-thin layers in order to avoid pin-hole leakage.

The electron beam is focused with a magnet coil after it passes through a pre-focusing aperture-lens stage. The focusing lens shown in FIG. 7 may be a Suzuki Precondenser Objective Lens or a Triplet Quadropole Lens. The beam can alternatively be focused by a quadropole magnetic lens (the quadropole can be a doublet or a triplet.) All magnetic devices with coil are housed outside the e-beam passage for easier evacuation and cooling. The aperture-lens can be a simple permanent magnet as part of the beam apparatus constructed inside the evacuated tube.

The x-ray generating film has a metal coating facing the evacuated region. As electrons enter the conductive layer, they would diffuse into a large area as shown in FIG. 4, and gradually lose energy. Electrons with peak energy can produce the peak x-ray photons, while electrons with lower energy cannot produce the peak x-ray photons. If only the peak x-ray photons are utilized for signal (electronically selected signal), then those diffused electrons with lower energy cannot contribute to the signal. In other words, by sharply focusing the e-beam at a small spot and by selecting only those photons with peak energy for signal, a very sharp x-ray spot can thus effectively be created. A selective detector that can produce the shadow image as well as electronically select photons with proper energy for signal is used.

THE X-RAY DETECTOR

The x-ray detector is designed to operate at the room temperature. A charge-coupled device (CCD) with low noise is advantageous. The usual CCD for optical photons has a very shallow depletion thickness, t. A small t is very inefficient for registering the photon signals as most photons would generate electron-hole pairs outside the depleted region and cannot be collected as a signal. Larger t, or a thicker depletion region can be generated by using a semiconductor with a higher resistivity. Pixel size s of the CCD is of the same order of magnitude of the thickness t. Small s and large t may create merged pixels, while large s and a small t would give a noisy pixel with inefficient photon collection. For a typical CCD, its metal gate, etc. can interfere with incident x-rays. As shown in FIG. 8, illuminating from the back of the device can not only avoid metal interference, but also using the back substrate to screen out the low energy photons. FIG. 8 shows the field-free region $x_{ff}$, the p-depletion region $x_p$ with acceptor concentration $N_A$, and the n-depletion region $X_n$ with donor concentration $N_D$. The electric field within $X_p$ and $x_n$ is generated through the voltages $V_{np}$ and $V_{fg}$. The backside reflecting field $E_b$ is provided by voltage $V_{bg}$. Backside illumination is illustrated. Front-side illumination is also possible and is advantageous in some applications.

A semiconductor with higher Z, such as a germanium or gallium-arsenic compound can capture x-ray photons far more effectively than that of silicon. Also a high Z doped (not lithium drifted) silicon would serve the same purpose. But for MOS devices for x-rays, a large t must be engineered into fabrication.

THE IMAGE

Signals from the CCD are digitized and all those which fall below a certain level are discriminated against, as discussed above. Only photons originating from a chosen beam spot are utilized for the shadow image.

Biological specimens are typically composed of low Z material which do not give rise to a shadow in x-rays. In order to enhance the image contrast, a differential mode of image construction can help to improve the contrast. Images are first digitized, one for the specimen and another without the specimen. As shown in FIG. 3, the difference of the two images give a better contrast.

Instead of electronically enhancing the contrast, a physical means to create better contrast is to incorporate high Z elements into the specimen. Iodine, for example, is broadly used in radio-immunoassay (RIA). I-125 has been used in enzymes, peptides, proteins, and the chemical interference of iodine is well understood. Another element bromine, in the molecule BrdU, can readily replace thymidine without biological toxicity. BrdU can be present in all kinds of molecules of nucleic acid. Just these two elements, iodine and bromine are useful for most of the biological activities. Other elements with high Z that were developed in the electron microscopy for contrast can also be utilized in the present x-ray microscopy.

It is contemplated that the inventive concepts herein described may be variously otherwise embodied, and it is intended that the appended claims be construed to include alternative embodiments of the invention except insofar as limited by the prior art.

I claim:

1. A method of investigating materials by the use of x-rays which comprises focusing an accelerated beam of electrons in an evacuated space on a metal foil facing said evacuated space, wherein the metal foil has a thickness of less than about 0.1 μm, the electron beam focused on said metal foil having a beam diameter of less than about 1000 Å incident on the metal foil, said metal foil being supported on a first surface of a support substrate which is substantially transparent to x-rays and has a second surface outside said evacuated space, said focused electron beam generating x-rays in said metal foil, placing a specimen of a material to be investigated adjacent to said second surface of said substrate in a position exposed to the x-rays generated in said metal foil, and selectively detecting from said specimen only x-rays selected from those having a peak energy or an energy close to the peak energy.

2. A method according to claim 1, wherein the beam of electrons is focused to a beam diameter of less than about 500 Å incident on the metal foil.

3. A method according to claim 1, wherein the beam of electrons is focused to a beam diameter of less than about 100 Å incident on the metal foil.

4. A method according to claim 1, wherein the beam of electrons is focused to a beam diameter of less than about 10 Å incident on the metal foil.

5. A method according to claim 1, wherein the metal foil is a coating of metal on said substrate.

6. A method according to claim 1, wherein a first signal from x-rays detected from said specimen, a second signal is obtained from x-rays detected from the metal foil and substrate in the absence of said specimen, and said second signal is digitally subtracted from said first signal, thereby obtaining a digitally encoded image of a region of the specimen.

7. A method according to claim 13, wherein an area of the metal foil is scanned by the beam of electrons, and a digitally encoded image of a region of the specimen is amplified and displayed by an electron beam in a cathode ray tube, said electron beam in the said cathode ray tube being scanned in synchronization with the scanning of the beam of electrons directed to the metal foil.

8. A method according to claim 1, wherein fluorescent x-rays emitted from said specimen are selectively detected.

9. A method according to claim 8, wherein fluorescent x-rays characteristic of a specific chemical element are detected and a signal is produced which is representative of the concentration of said specific chemical element in said specimen.

10. A method according to claim 9, wherein the energy of the accelerated beam of electrons is substantially the same as the energy of the fluorescent x-rays characteristic of said specific chemical element.

11. A method according to claim 10, wherein the energy of the accelerated beam of electrons is sequentially changed to provide a series of different energies corresponding to different energies of fluorescent x-rays characteristic of different chemical elements, and signals are produced which represent the concentration of a plurality of chemical elements in said specimen.

12. A method according to claim 11, wherein over a period of time different signals are produced representing changing concentrations of said different chemical elements in said specimen.

13. A method according to claim 11, wherein an area of 370 the metal foil is scanned by the accelerated beam of electrons and signals are produced representative of the concentrations of a plurality of different elements throughout a region of said specimen.

14. A method according to claim 12, wherein an area of the metal foil is scanned by the accelerated beam of electrons and signals are produced representative of changing concentrations of different elements throughout of region of the specimen.

15. A method according to claim 1, wherein the specimen is a biological specimen which is investigated under ambient conditions of the environment without being subjected to high radiation dosage or evacuation.

16. An apparatus for investigating materials by the use of x-rays, which comprises:
 a chamber for being maintained under vacuum;
 said chamber having a wall which has an aperture in which is mounted a support substrate composed of a material substantially transparent to x-rays, said support substrate having a first surface facing the interior of said chamber and a second surface outside said chamber, said first surface of the support substrate having thereon a metal foil, said metal foil having a thickness of less than about 0.1 $\mu$m, exposed to the interior of the chamber;
 means for focusing a beam of electrons within said chamber on said metal foil to a beam diameter of less than about 1000 Å incident on the metal foil;
 means for positioning a specimen outside said chamber adjacent to said second surface of the support substrate; and
 at least one x-ray detector positioned to detect x-rays leaving said specimen, said x-ray detector being an energy dispersive x-ray detector capable of selecting and recording peak energy and energies close to peak energy.

17. An apparatus according to claim 16, which further comprises means for producing and accelerating a beam of electrons within said chamber along a beam path.

18. An apparatus according claim 17, wherein said chamber is an elongated hollow body having first and second end walls, with said means for producing and accelerating said beam of electrons being adjacent to said first end wall, and said support substrate being mounted in said second end wall, said beam path extending along a lengthwise axis in a downstream direction, from said means for producing and accelerating said beam of electrons to said metal foil.

19. An apparatus according to claim 18, wherein an x-ray detector is positioned downstream from said means for positioning a specimen, in the path of x-rays transmitted from said specimen, and said means for positioning a specimen and said x-ray detector are disposed in alignment with said axis.

20. An apparatus according to claim 19, having another x-ray detector which is positioned out of alignment with said axis, substantially out of the path of x-rays transmitted through said specimen and in the path of fluorescent x-rays emitted from said specimen.

21. An apparatus according to claim 18, wherein an x-ray detector is positioned out of alignment with said axis, substantially out of the path of x-rays transmitted through said specimen and in the path of fluorescent x-rays emitted from said specimen.

22. An apparatus according to claim 16, further comprising an axial symmetric diffractor for directing x-rays having energies close to peak energies towards said x-ray detector while blocking the passage of lower energy x-rays, said diffractor being located between said means for positioning a specimen and said x-ray detector and being axially in alignment with said axis.

23. An apparatus according to claim 16, wherein said energy dispersive x-ray detector is a charge-coupled device.

24. An apparatus according to claim 18, further comprising:
 means for scanning said beam of electrons over an area of the metal foil,
 means for amplifying a signal representative of detected x-rays;
 means for converting the amplified signal into a digitally encoded image of a scanned area;
 means for amplifying and displaying said image, said means for amplifying and displaying comprising a cathode ray tube for being scanned by an electron beam, in synchronization with the scanning of the metal foil.

25. An apparatus according to claim 21, wherein the means for producing and accelerating said beam of electrons includes means for dynamically scanning the energy of said beam of electrons.

26. An apparatus according to claim 20, wherein the x-ray detector is an energy dispersive and energy discriminating detector for selectively detecting fluorescent x-rays characterisitic of specific chemical elements.

* * * * *